United States Patent [19]

Shah

[11] Patent Number: 4,872,483
[45] Date of Patent: Oct. 10, 1989

[54] CONVENIENTLY HAND HELD SELF-CONTAINED ELECTRONIC MANOMETER AND PRESSURE MODULATING DEVICE

[75] Inventor: Nyan S. Shah, Mentor, Ohio

[73] Assignee: International Medical Products, Inc., Mentor, Ohio

[21] Appl. No.: 140,121

[22] Filed: Dec. 31, 1987

[51] Int. Cl.$^4$ ............................................. A61M 16/04
[52] U.S. Cl. ........................................ 137/557; 73/753; 128/207.15; 604/97; 604/99; 604/100
[58] Field of Search .................... 137/557; 251/367; 73/753, 708; 116/266, DIG. 17; 128/207.15; 604/97, 99, 100

[56] References Cited

U.S. PATENT DOCUMENTS

| | | | |
|---|---|---|---|
| 4,038,532 | 7/1977 | Burris et al. | 73/753 X |
| 4,307,617 | 12/1981 | Greer et al. | 73/753 |
| 4,369,660 | 1/1983 | Lentz et al. | 73/753 |
| 4,383,534 | 5/1983 | Peters | 128/207.15 X |
| 4,399,836 | 8/1983 | de Vesterre et al. | 251/367 X |
| 4,501,273 | 2/1985 | McGinnis | 128/207.15 |
| 4,509,514 | 4/1985 | Brain | 128/207.15 |
| 4,526,196 | 7/1985 | Pistillo | 137/557 |
| 4,583,917 | 4/1986 | Shah | 417/63 |
| 4,762,125 | 8/1988 | Leiman et al. | 128/207.15 |

Primary Examiner—John Rivell
Attorney, Agent, or Firm—Hill, Van Santen, Steadman & Simpson

[57] ABSTRACT

A conveniently hand held self-contained electronic manometer assembly small enough to be held in the palm of one hand comprises a structure having a pressure sensor arranged to be exposed to a site at which there is pressure to be monitored, and an electronic system carried by the structure translates pressure sensed by the sensor into a digital display carried by the structure. The structure may also carry a pressure modulating device such as a digital pump and pressure relief valve or a syringe arrangement.

7 Claims, 2 Drawing Sheets

CONVENIENTLY HAND HELD SELF-CONTAINED ELECTRONIC MANOMETER AND PRESSURE MODULATING DEVICE

BACKGROUND OF THE INVENTION

This invention relates to a new and improved hand held electronic manometer and is more particularly concerned with such a manometer comprising a self-contained assembly which may have a pressure modulating device.

Although, as will become apparent, the present invention may serve advantageously for determining and modulating fluid pressure in many situations, an important utility resides in providing for convenient, substantially accurate monitoring in the course of various intra-body surgical procedures, information as to fluid pressure, either gas or liquid, for any of several reasons such as safety of involved body tissues, surgical performance, and the like. For example, where anesthetic is administered to a patient by using an endotracheal tube having an inflatable cuff which is inflated by a source of pressurized air, proper inflation of the cuff should be monitored to assure that the endotracheal tube is properly restrained against slippage but not over-inflated to the point of damage of the mucosal wall of the trachea. In another procedure involving heart chamber and related arterial pressure, the pressure should be critically monitored, and may also require modulation.

Hand held gas pressure regulating and monitoring devices, utilizing a mercury column for visually indicating pressure such as in endotracheal tube procedures, are disclosed in Pistillo U.S. Pat. No. 4,526,196 and Shah U.S. Pat. No. 4,583,917. While the devices disclosed in those patents provide exceptionally desirable small, convenient, hand held units, the mercury for translating pressure into a mercury column pressure gauge requires that the device be maintained in a reasonably vertical position for attaining the desired accuracy of pressure readout during use of the device. Further, although ample safety precautions are built into the patented devices, there is sometimes resistance to use of the devices in surgical procedures for fear of mercury contamination.

SUMMARY OF THE PRESENT INVENTION

An important object of the present invention is to improve pressure monitoring by means of a conveniently hand held electronic manometer assembly.

Another object of the invention is to provide a new and improved method of and means for monitoring critical fluid pressures by use of an electronic hand held compact manometer assembly which may also possess pressure regulating and modulating means.

A further object of the invention is to provide new and improved conveniently hand held electronic manometer and pressure regulating and modulating device in a self-contained small size assembly.

Pursuant to the principles of the present invention, there is provided a new and improved conveniently hand held electronic manometer assembly small enough to be held in the palm of one hand and comprising a structure including a pressure sensor, means for exposing said sensor to a site at which there is a pressure to be monitored, and electronic means on said structure for translating pressure sensed by the said sensor into a digital display carried by said structure.

The structure of said electronic manometer assembly may have means defining a communication passage, a coupling device on the structure for attachment to a pressure conveying conduit leading from the passage to an enclosed site at which there is a fluid pressure to be monitored, and the sensor being exposed to the pressure in the communication passage.

Further, the electronic manometer assembly as set forth may include a pressure modulating means.

The present invention also provides a new and improved method of electronic pressure monitoring for the practice of which the foregoing electronic manometer assembly is especially adapted

BRIEF DESCRIPTION OF THE DRAWINGS

Other objects, features and advantages of the present invention will be readily apparent from the following description of certain representative embodiments thereof, taken in conjunction with the accompanying drawings, although variations and modifications may be effected without departing from the spirit and scope of the novel concepts embodied in the disclosure, and in which.

DETAILED DESCRIPTION

Figure 1:
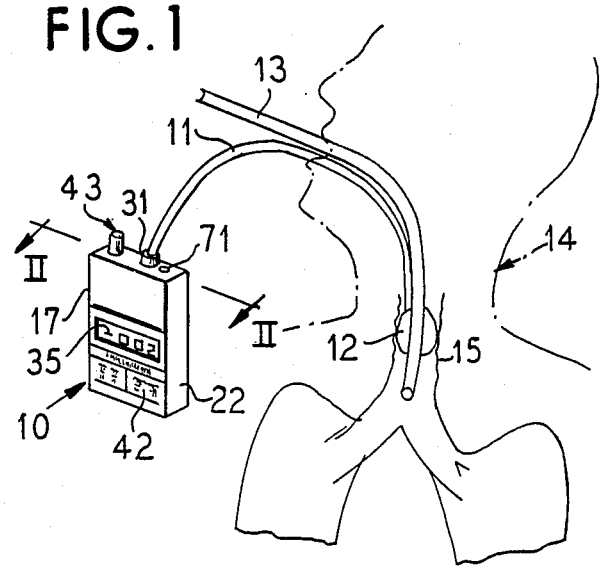
FIG. 1, is a perspective view, partially in phantom of an endotracheal tube in conjunction with which there is a pressure monitoring assembly, including a pressure modulating device, embodying the present invention.

By way of example, a conveniently hand held electronic manometer assembly instrument 10 (FIGS. 1 to 4) embodying the present invention is adapted to be connected as by means of a flexible tube 11 with a point of gas pressure to be monitored and modulated, such as an inflatable bulb or cuff 12 which provides a sealed enclosure surrounding an endotracheal tube 13.

In use, the endotracheal tube 13 is inserted through the mouth of a patient 14 and is advanced into the trachea 15 where the inflatable cuff 12 is inflated to a predetermined pressure to retain the endotracheal tube 13 within the trachea 15. It is important to maintain the pressure within the cuff 12 as nearly as practical at about 25 cmH$_2$O in order to avoid damage to the mucosal wall of the trachea 15. For various reasons the pressure in the cuff 12 may increase due to expansion of the air in the cuff without additional air input, as for example, where the material of the cuff may permit anesthetic delivered the lungs of the patient through the duct of the tube 13 to pass through the wall of the cuff and thus increase the intracuff pressure.

Desirably, the assembly 10 comprises a compact, self-contained structure within a body, including a vertically elongated housing 17 which is desirably molded from a rigid plastic material such as acrylic. For assembly convenience, the housing 17 comprises a pair of complementary, flanged front and rear panels 18 and 19 (FIG. 4) attached at their side flanges by tongue and groove means 20 and thereby providing a left side 21 and a right side 22 for the housing. Continuations of the side flanges along the lower ends of the panels 18 and 19 cooperate to provide a bottom wall 23 for the housing. A housing top wall 24 is provided by a panel 24 which is joined with the upper portions of the wall panels 18 and 19 as by tongue and groove means 25. Bolts 26 hold the panels 18 and 19 together separably.

Within the upper portion of the housing 17 and contiguous to the top wall 24 is mounted a core block providing a manifold 27. Proper vertical position of the manifold 27 may be maintained by a tongue and groove connection 28 with the side walls 21 and 22. Within the manifold 27 is defined a communication passage 29, and a luer connection nipple or tip 30 provides means for removably attaching the proximal end of the duct 11 to the manifold. An annular upstanding protector 31 surrounds the tip 30 in spaced relation.

At the lower end of the passage 29, a fluid pressure sensor 32 carried by the manifold 27 is exposed to any fluid pressure in the passage. In this instance, the sensor 32 is an electronic transducer of the kind which may be procured, for example, from Servo Flow, Inc., Boston, Mass., and identified as their Fijicura No. FPM05-PG. The transducer 32 has terminals 33 which are electrically connected to a printed circuit board 34 below the manifold 27. The board is operatively connected with an LCD digital display volt meter readout device 35 (FIGS. 1 and 3) such as may be obtained from VGI, Inc. of San Jose, Cal., as their Model VK1000. An on/off switch 37 accessible through an opening 38 in the side wall 21 permits control of the electronic circuitry. Conventional range and zero adjustment means may be provided. Electrical power for the electronic circuitry is derived from a small battery 39 such as of 9 volt capacity which is replaceably coupled with the circuitry as by means of a terminal member 40. Dielectric cushions 41 may be provided for holding the battery 39 steady within the lower portion of the housing under the board 34. A low battery signal lamp 39a may be carried by the panel 18, or may be a part of the LCD volt meter device 35.

Figure 3:
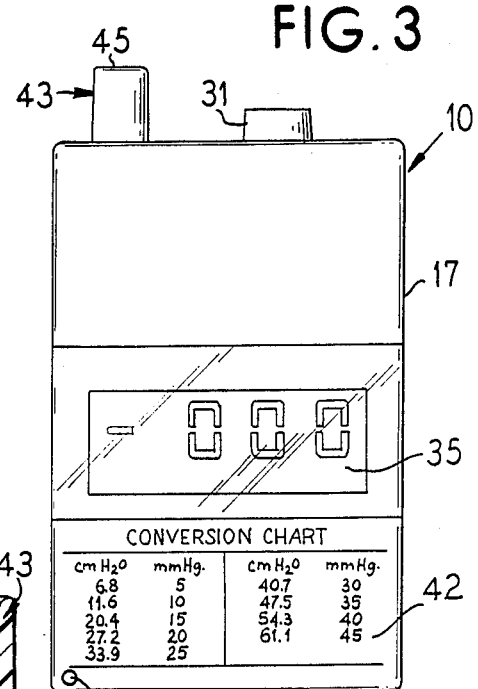
FIG. 3 is a front elevational view of the self-contained manometer and pressure modulating assembly of FIGS. 1 and 2.
Figure 2:
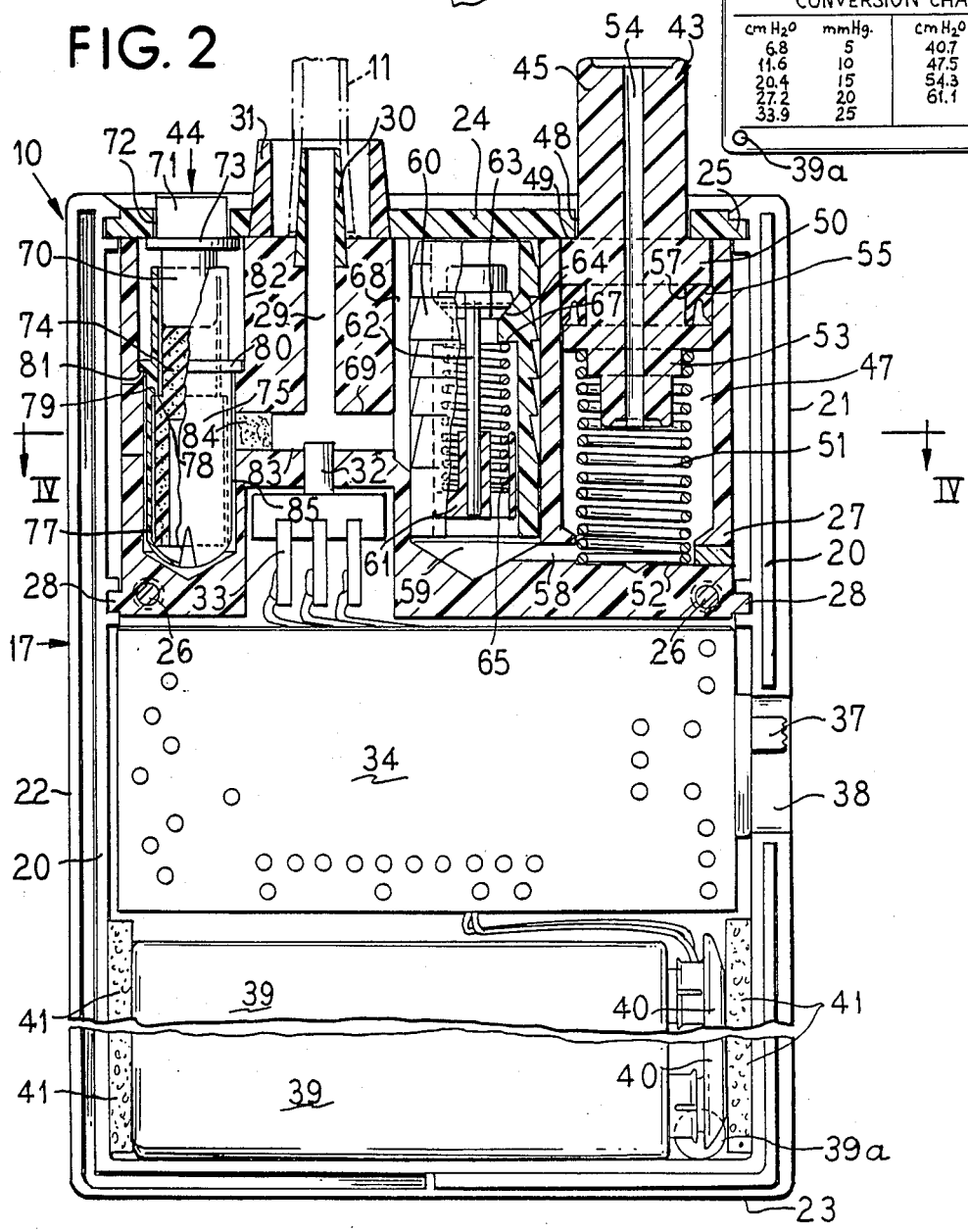
FIG. 2 is an enlarged vertical sectional detail view taken substantially along the line II—II in FIG. 1.

It will thus be apparent that pressure in the passage 29 sensed by the transducer 32 can be read on the digital display 35. The readout may be according to a cm H20 scale, and since it may be desirable to have the readout converted to a millimeter mercury scale, a conversion chart 42 is provided on the front wall face of the housing 10 adjacent to the digital display 35, as best seen in FIG. 3.

Means are provided for regulating, that is, modulating the pressure within the enclosed pressure area wherein fluid pressure is to monitored, such as the endotracheal cuff 12. To this end, digitally operable pressurizing pump means 43 and digitally operable pressure relief valve means 44 are carried by the housing body structure IO on and within the manifold 27 and communicating with the passage 29.

In a desirable arrangement, the pressurizing means 43 comprises a thumb depressable spring loaded pump plunger 45 which is accommodated within a vertical blind end bore 47 that opens through the top of the manifold 27. The plunger 45 has a reduced diameter upper end portion projecting slidably through a clearance hole 48 in the cover plate 24. The area of the plate 24 about the hole 48 provides a stop surface against which an annular upwardly facing shoulder 49 on an enlarged diameter portion 50 of the plunger engages.

Normally the plunger 45 is biased upwardly toward the stop surface by means of a coiled compression spring 51 which thrusts at its lower end into a centering well 52 at the lower end of the bore 47. At its upper end the spring 51 thrusts against a stop shoulder lower end of the enlarged diameter portion 50 of the plunger. A downwardly projecting centering boss 53 on the plunger maintains the spring 51 centered. A pressure relief central bore 54 extends throughout the length of the plunger 45 and is adapted to be closed by the thumb of the person who is using the manometer instrument when it is desired to pnumatically pressurize the enclosed area such as the endotracheal balloon 12 with which the instrument is connected. A pressure seal 55 is mounted in an annular seal groove 57 in the perimeter of the enlarged body portion 50 of the plunger 45.

Air pressure generated by manipulation of the pump plunger 45 passes from the lower end of the pressure chamber of the bore 47 to the lower blind end of a vertical pressure chamber bore 59 within which is mounted a check valve 60 of the kind having a spider 61 to which is connected by a pin 62 a valve head 63 that engages a generally upwardly facing valve seat 64, against which the valve head is biased into check valve-closing relation by means of a compression spring 65 thrusting downwardly against the spider 61 and upwardly against a shoulder 67 on the tubular housing of the check valve. The air pressure raises and passes the check valve head 63 and is conducted by means of a vertical passage 68 connected at its lower end with a passage branch 69 leading into the lower end of the vertical communication passage 29 just above the trandsucer 32.

If the digital display 35 shows that the pressure in the passage 29 is higher than desired, the relief valve 44 is adapted to be operated for relieving the pressure down to the desired value. A simple form of the relief valve 44 comprises a digitally manipulatable plunger 70 having a button head 71 projecting upwardly through a hole 72 in the cover 24 against which a stop collar 73 at the lower end of the head 71 is normally biased. A sponge rubber member 74 is carried within an elongated shell 75 partially crimped closed at the bottom and having vertical internal channels 77 communicating with the partially open bottom of the shell 75 to bypass the rubber member 74 to an upwardly facing annular valve shoulder 78 normally biased against a downwardly facing internal annular valve seat 79 provided by the shell 75. At its upper end, the shell 75 has a stop collar 80 that thrusts under downward bias against an upwardly facing annular shoulder 81 within bore 82 accommodating the relief valve.

When it is desired to relieve pressure from the communication passage 29, the plunger head 71 is depressed for opening the relief valve 44 which permits air pressure to escape from the passage 29 through a branch passageway 83 and a muffle filter 84 therein into a restricted flow path 85 provided by a narrow clearance in the bore 82 about the shell 75. Thereby the muffled air travels by a relatively tortuous path from the communication passage 29 downwardly past the relief valve shell 75 and through the semi-open lower end of the shell and then upwardly through the relief valve channels 77 and escapes through the opening 72 which has been opened by depressing of the stop collar 73. This arrangement provides relatively fine incremental pressure relief control which is especially advantageous where the instrument is used in a surgical procedure.

The instrument IO is especially advantageous for medical technicians who can carry the same handily in a pocket of a smock or apron, from which the instrument can be quickly retrieved and used while carried in one hand. The pressure pump plunger 45 or the relief valve plunger head 71 can be easily manipulated by the thumb of the instrument-carrying hand. In a preferred form, the overall dimensions of the instrument 10 can be accommodated within the housing 17 having dimensions of about 2½ inches wide by 4 inches long and 1 inch thick.

Figures 4, 5:
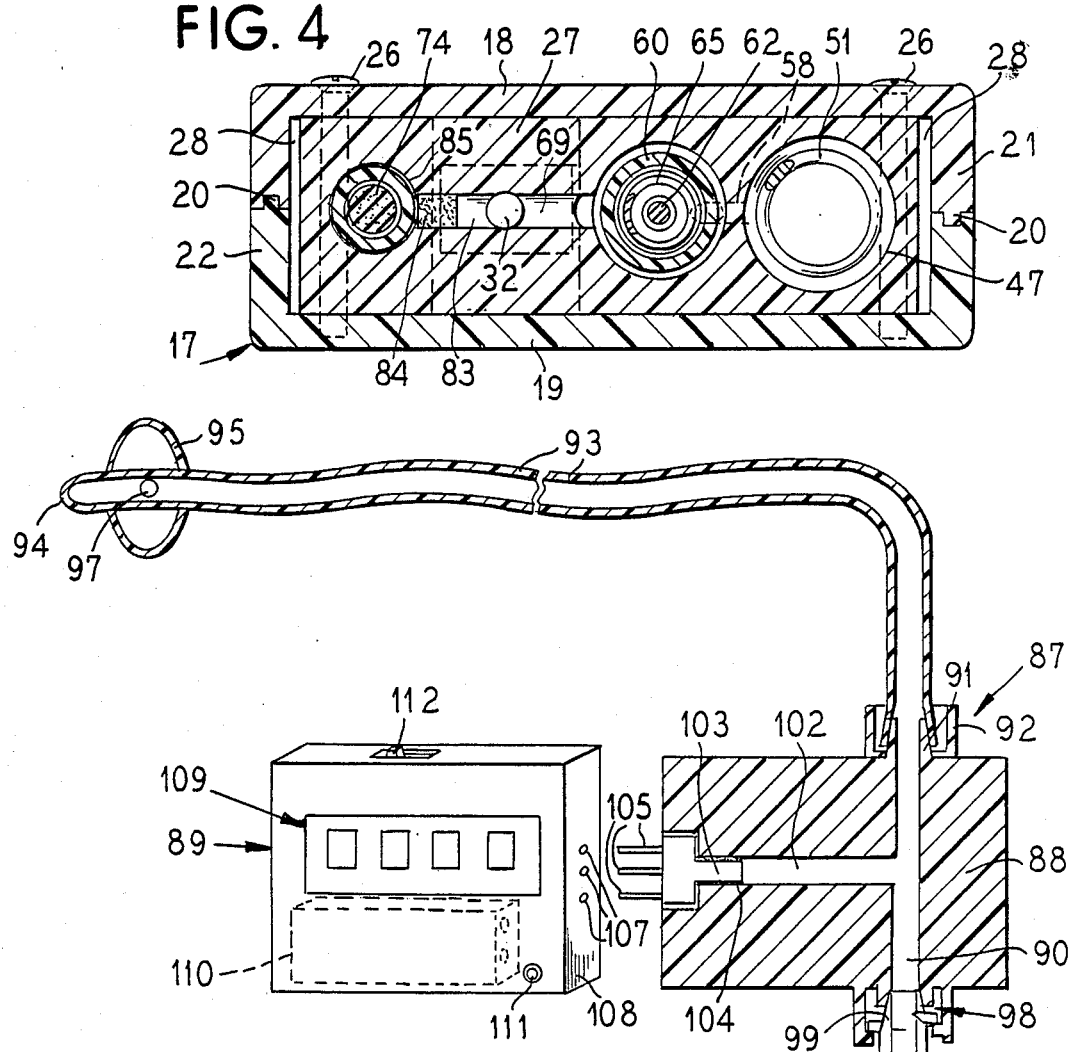
FIG. 4 is a horizontal sectional detail view taken substantially along the line IV-IV in FIG. 2.
FIG. 5 is a perspective and elevational view, partially in section, showing a modification of the electronic manometer and pressure modulating device according to the present invention.

A simple embodiment of the present invention comprising a conveniently hand held electronic manometer assembly instrument 87, as shown in FIG. 5, is especially adapted for liquid pressure monitoring. This comprises a structure including a body 88 providing a manifold constructed and arranged for removable attachment to an electronic unit 89.

In a preferred construction, the manifold 88 comprises a panel-like molded plastic block having a pressure communication passage 90 extending therethrough from side to side. At one end of the passage 90, a luer nipple 91 surrounding by an upstanding annular protector 92 is adapted to have connected thereto a catheter 93 having a closed end 94 about which is an integral cuff 95 in communication with the channel in the catheter through a port 97.

At the opposite end of the communication passage 90, the manifold 88 carries a luer lock means 98 for attaching in fluid tight relation to the manifold a discharged nipple 99 of a syringe barrel 100 which has a piston 101 adapted for injecting liquid from the syringe through the passage 90 into the catheter 93 for pressurizing the cuff 95. For monitoring the pressure in the passage 90, a branch passage 102 in the manifold 88 leads from the passage 90 to a pressure sensor transducer 103 which is desirably permanently secured to the manifold as by means of adhesive 104. Transducer contact terminal pins 105 serve as means for connecting the manifold to the electronic unit 89. Receptacle pin sockets 107 in one side of a housing 108 of the electronic unit 89 are adapted to receive the pins 105 frictionally.

The electronic means within the unit 89 are desirably similar to the electronic means in the manometer assembly instrument 10, comprising a printed circuit board (not shown) connected to an LCD digital display volt meter readout device 109 similar to the device 35, with electrical power for the electronic circuit rederived from a battery 110 which is connected to a low battery warning light 111, which may be part of the device 35. An on/off switch 112 controls the electronic circuitry in the unit 89. By having the manifold 88 separably connectable to the electronic unit 89, the manifold 88 and its aperternances may be disposably detached from the unit 89 after, for example, a medical or surgical procedure in which the instrument is used. Procedures in which the instrument 87 may be advantageously used comprise cardiac, neurological, angioplastic catheterisations, vein or artery pressure monitoring, and the like, and wherein it is highly desirable to be able to monitor the pressure at the procedure site continuously, and when desirable, effect pressure modulating.

It will be understood that variations and modifications may be effected without departing from the spirit and scope of the novel concepts of this invention.

I claim as my invention:

1. An electronic manometer assembly for use in monitoring pressure at a site in the body of a patient comprising:
    a numerical read-out unit having a size adapted to be conveniently held in the palm of the hand of a user, said numerical read-out unit having an output passage therein;
    manually digitally operable pump means contained in said numerical read-out unit in fluid communication with said output passage for generating a pressure head;
    delivery means in fluid communication with said output passage and adapted for insertion in a patient for delivering said pressure head from said output passage to said site in said patient said delivery means terminating in an enclosed, inflatable cuff;
    electronic pressure transducer means in said numerical read-out unit in fluid communication with said output passage for generating an electrical signal corresponding to the pressure in said cuff of said delivery means;
    electronic display means in said numerical read-out unit electrically connected to said transducer means for visually displaying a number corresponding to said electrical signal and thus to said pressure in said cuff of said delivery means; and
    power supply means contained within said numerical read-out unit and electronically connected to said electronic pressure transducer means and to said electronic display means for supplying electrical power thereto.

2. An electronic manometer assembly as claimed in claim 1 further comprising:
    a one-way check valve disposed in said electronic read-out unit between said manually digitally operable pump means and said output passage which permits delivery of said pressure head from said manually digitally operable pump means through said output passage to said delivery means.

3. An electronic manometer assembly as claimed in claim 1 further comprising:
    a manually digitally operable pressure relief valve disposed in said read-out unit in fluid communication with said output passage which, upon actuation, opens said output passage to the atmosphere to permit deflation of said cuff.

4. An electronic manometer assembly as claimed in claim 1 further comprising:
    a table attached to an exterior of said numerical read-out unit for converting between pressure measured in centimeters of $H_2O$ and millimeters of Hg.

5. An electronic manometer assembly for use in monitoring pressure at a site in the body of a patient comprising:
    a manifold unit having a passage therein adapted for connection to a manually operable external means for generating a pressure head;
    delivery means in fluid communication with said passage in said manifold unit and adapted for insertion in a patient for deliverying said pressure head from said passage to said site in said patient, said delivery means terminating in a enclosed, inflatable cuff;
    electronic pressure transducer means in said manifold unit in fluid communication with said passage for generating an electrical signal corresponding to the pressure in said cuff of delivery means;

an electronics unit having an electronic numerical display for visually displaying a number corresponding to said electrical signal from said electronic pressure transducer and thus to said pressure in said cuff of said delivery means;

an electrical power source in said electronical unit; and means for mechanically and electrically connecting said electronic unit and said manifold unit with said electronic pressure transducer being electrically connected to said power source and to said numerical display means, said electronic unit and said manifold unit, when connected, having a size adapted to be conveniently held in the palm of the hand of a user.

6. An electronic manometer assembly as claimed in claim 5, wherein said passage in said manifold unit is adapted to receive a syringe as said manually operable external means for generating a pressure head.

7. An electronic manometer assembly as claimed in claim 5, wherein said means for mechanically and electrically connecting said manifold unit and said electronic unit comprises a plurality of contact prongs of said electronic pressure transducer means, and a like plurality of receptacles for said prongs in said electronic unit.

* * * * *

REEXAMINATION CERTIFICATE (1913th)
United States Patent [19]
Shah

[11] B1 4,872,483
[45] Certificate Issued Jan. 26, 1993

[54] CONVENIENTLY HAND HELD SELF CONTAINED ELECTRONIC MANOMETER AND PRESSURE MODULATING DEVICE

[75] Inventor: Nyan S. Shah, Mentor, Ohio

[73] Assignee: International Medical Products, Inc., Mentor, Ohio

Reexamination Request:
No. 90/002,015, Apr. 30, 1990

Reexamination Certificate for:
Patent No.: 4,872,483
Issued: Oct. 10, 1989
Appl. No.: 140,121
Filed: Dec. 31, 1987

[51] Int. Cl.⁵ .......................................... A61M 16/04
[52] U.S. Cl. ..................... 137/557; 73/753; 128/207.15; 604/97; 604/99; 604/100
[58] Field of Search ............ 137/557; 251/367; 73/708, 753; 116/266, DIG. 17; 128/207.15; 604/97, 99, 100

[56] References Cited

U.S. PATENT DOCUMENTS

| | | | |
|---|---|---|---|
| 4,038,532 | 7/1977 | Burris et al. | 73/753 X |
| 4,250,759 | 2/1981 | Vago | 73/723 |
| 4,307,617 | 12/1981 | Greer et al. | 73/753 |
| 4,369,660 | 1/1983 | Lentz et al. | 73/753 |
| 4,383,534 | 5/1983 | Peters | 128/207.15 X |
| 4,399,836 | 8/1983 | de Vesterre et al. | 251/367 X |
| 4,501,273 | 2/1985 | McGinnis | 128/207.15 |
| 4,509,514 | 4/1985 | Brain | 128/207.15 |
| 4,526,196 | 7/1985 | Pistillo | 137/557 |
| 4,704,901 | 11/1987 | Rocco | 73/146.8 |
| 4,762,125 | 8/1988 | Leiman et al. | 128/207.15 |

OTHER PUBLICATIONS

Medical Electronics, Cuffcheck Brochure, Date unknown.
Medical Electronics Corp., Cuffcheck, AARTimes, Aug. 1983, pp. 131 and 152.
Medical Electronics Corp., Cuffcheck, Respiratory Therapy, Jan./Feb. 1984, pp. 28 and 88.
Medical Electronics Corp., Cuffcheck, Respiratory Therapy, Mar./Apr. 1984, p. 28.
Portex, Inc., Cuffcheck, respiratory Therapy, May/-Jun. 1984, p. 62.
Medical Electronics Corp., Cuffcheck, Respiratory Care, Dec. 1983, p. 1622.
Portex, Inc. Brochure, Date unknown.

*Primary Examiner*—John Rivell

[57] ABSTRACT

A conveniently hand held self-contained electronic manometer assembly small enough to be held in the palm of one hand comprises a structure having a pressure sensor arranged to be exposed to a site at which there is pressure to be monitored, and an electronic system carried by the structure translates pressure sensed by the sensor into a digital display carried by the structure. The structure may also carry a pressure modulating device such as a digital pump and pressure relief valve or a syringe arrangement.

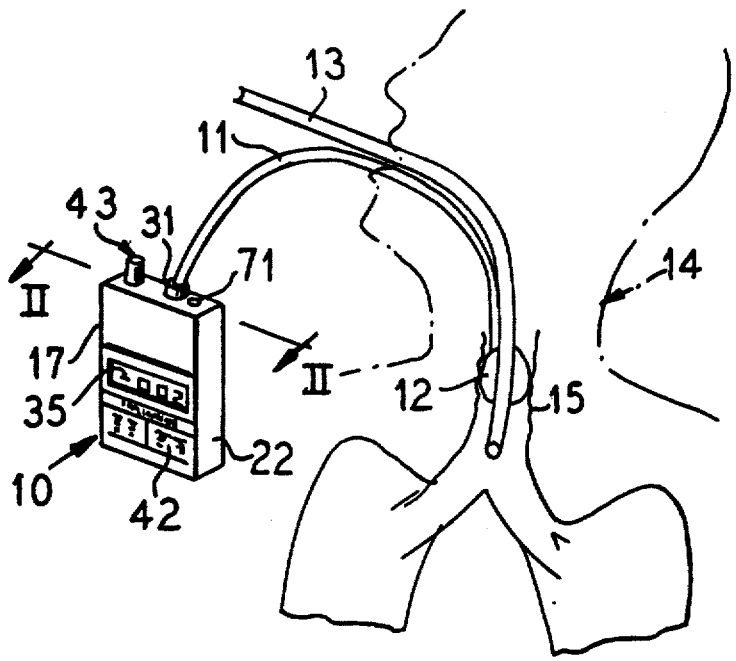

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 5-7 is confirmed.

Claims 1-4 are cancelled.

* * * * *